US 11,819,635 B2

(12) United States Patent
Zhang et al.

(10) Patent No.: US 11,819,635 B2
(45) Date of Patent: Nov. 21, 2023

(54) STEERABLE CATHETER SUITABLE FOR LEFT-HAND OPERATION

(71) Applicant: Hangzhou Wei Qiang Medical Technology Co., Ltd, Zhejiang (CN)

(72) Inventors: Tingchao Zhang, Zhejiang (CN); Yang Li, Zhejiang (CN); Quanjie Jiang, Zhejiang (CN); Weiguo Fu, Zhejiang (CN)

(73) Assignee: Hangzhou Wei Qiang Medical Technology Co., Ltd, Hangzhou (CN)

( * ) Notice: Subject to any disclaimer, the term of this patent is extended or adjusted under 35 U.S.C. 154(b) by 637 days.

(21) Appl. No.: 16/473,247

(22) PCT Filed: Dec. 27, 2017

(86) PCT No.: PCT/CN2017/119064
§ 371 (c)(1),
(2) Date: Jun. 25, 2019

(87) PCT Pub. No.: WO2018/130074
PCT Pub. Date: Jul. 19, 2018

(65) Prior Publication Data
US 2021/0338983 A1    Nov. 4, 2021

(30) Foreign Application Priority Data

Jan. 16, 2017    (CN) .......................... 201710032525.7

(51) Int. Cl.
*A61M 25/01*    (2006.01)
*A61M 39/10*    (2006.01)

(52) U.S. Cl.
CPC .... *A61M 25/0147* (2013.01); *A61M 25/0136* (2013.01); *A61M 39/1011* (2013.01);
(Continued)

(58) Field of Classification Search
CPC .......... A61M 25/0136; A61M 25/0147; A61M 2025/015; A61M 2025/09116;
(Continued)

(56) References Cited

U.S. PATENT DOCUMENTS

| 5,472,017 A | * | 12/1995 | Kovalcheck | ...... A61M 25/0136 138/120 |
| 2006/0142694 A1 | * | 6/2006 | Bednarek | ............... A61B 5/287 604/95.04 |

(Continued)

FOREIGN PATENT DOCUMENTS

| CN | 106730246 A | | 5/2017 |
| CN | 206809529 U | * | 12/2017 |

(Continued)

OTHER PUBLICATIONS

International Search Report of PCT Patent Application No. PCT/CN2017/119064 dated Mar. 26, 2018.
(Continued)

*Primary Examiner* — Nathan R Price
*Assistant Examiner* — Mark A Igel

(57) ABSTRACT

A steerable catheter suitable for left-hand operation includes a tube, a handle assembly, and a Luer connector. The handle assembly comprises a holding handle, a slide mechanism, and a slide control mechanism; a proximal end of the tube passes through a cavity of the holding handle to be connected with the Luer connector; the slide mechanism comprises a slide base body, and a slide member axially sliding along the holding handle and fitted on the slide base body; the slide member is fixedly connected to a pull wire; the slide control mechanism comprises a connecting member connected with the slide member, and a drive adjustment member connected with the connecting member and adjusting the position of the slide member; the drive adjustment
(Continued)

member is provided at the proximal end of the holding handle for convenient left hand operation.

11 Claims, 9 Drawing Sheets

(52) U.S. Cl.
CPC ............... *A61M 2025/015* (2013.01); *A61M 2039/1033* (2013.01); *A61M 2205/586* (2013.01)

(58) Field of Classification Search
CPC ...... A61M 2025/09125; A61M 25/015; A61M 25/0133; A61M 25/136; A61M 39/1011; A61M 2039/1033; A61M 2205/586
See application file for complete search history.

(56) References Cited

U.S. PATENT DOCUMENTS

| | | | | |
|---|---|---|---|---|
| 2010/0160858 A1* | 6/2010 | Fischer | ............ | A61M 25/0136 604/95.04 |
| 2016/0058974 A1* | 3/2016 | Kimmel | ............ | A61M 25/0136 600/417 |
| 2020/0121363 A1* | 4/2020 | Fu | ............ | A61B 17/3478 |

FOREIGN PATENT DOCUMENTS

| | | | | | |
|---|---|---|---|---|---|
| CN | 206809529 | U | | 12/2017 | |
| CN | 113521498 | A | * | 10/2021 | |
| EP | 2465568 | A1 | | 6/2012 | |
| GB | WO 2005021077 | A1 | * | 3/2005 | ........ A61M 25/0147 |
| WO | 2005021077 | A1 | | 3/2005 | |
| WO | WO-2005021077 | A1 | * | 3/2005 | ........... A61B 17/435 |
| WO | WO-2019024726 | A1 | * | 2/2019 | |

OTHER PUBLICATIONS

Written Opinion of the International Searching Authority of PCT Patent Application No. PCT/CN2017/119064 dated Mar. 26, 2018.
Extended European Search Report of counterpart European Patent Application No. 17891071.7 dated Dec. 2, 2019.
Examination report of counterpart European Patent Application No. 17891071.7 dated Jan. 25, 2022.
First Office Action of counterpart Chinese Patent Application No. 201710032525.7 dated Jun. 20, 2018.
Second Office Action of counterpart Chinese Patent Application No. 201710032525.7 dated Feb. 27, 2019.
Notice of Allowance of counterpart Chinese Patent Application No. 201710032525.7 dated Jul. 5, 2019.
Second Office Action of counterpart European Patent Application No. 17891071.7 dated Jul. 6, 2022.
Third Office Action of counterpart European Patent Application No. 17891071.7 dated Jan. 26, 2023.

* cited by examiner

STEERABLE CATHETER SUITABLE FOR LEFT-HAND OPERATION

TECHNICAL FIELD

The present invention belongs to the technical field of medical instruments, and relates to a steerable catheter, in particular to a steerable catheter suitable for left-hand operation.

BACKGROUND

The interventional surgery is a medical technology that has been rapidly developed and promoted in recent years since it has less damage to the human body and can effectively shorten the operation time. A catheter, serving as an auxiliary instrument for the interventional surgery, is mainly used for providing a tunnel for the guide wire. The guide wire is introduced into the target blood vessel by directing the head end of the catheter to an inlet of the target blood vessel through adjustment of the distal end of the catheter. Depending on the intended use of the catheter, the distal end of the catheter is pre-formed into a different bending shape to accommodate the anatomical morphology of a particular lesion, facilitating the alignment of the distal end of the catheter to the lesion in a human body, the catheter being such as a renal artery catheter, a radial artery catheter, a crossover catheter, etc. However, due to the individualized differences in the physiological anatomy of the human body, the pre-formed catheter cannot fully adapt to all clinical requirements. Therefore, in the prior art a catheter having an adjustable-bend end arises, and the distal end of the catheter can be repeatedly bent from an angle to a different angle by controlling the handle, so to accommodate different physiological anatomical morphologies.

For all of the steerable catheters in the prior art, free bending of the distal end of the tube is achieved by controlling the handle. During the surgical procedure of superselecting a target blood vessel, an operator usually repeatedly adjusts the bending of the distal end of the tube according to the structural morphology of the target blood vessel until the bending angle conforms to the physiological structural characteristics of the target blood vessel. Then, the bending angle of the distal end of the tube is locked, the port at the head end of the tube is aligned with the inlet of the target blood vessel by repeatedly twisting the tube, and finally the guide wire enters the target blood vessel along the tube by controlling the guide wire at the proximal end of the handle.

There is a straight steerable catheter in the prior art, a driving component on a handle of the catheter is located between a handle holding portion (for holding the handle) and the tube, and a guide-wire accessing hole is disposed at the proximal end of the handle. During the surgical procedure of superselecting a target blood vessel with a guide wire, an operator generally uses the right hand to control the guide wire, and also needs the right hand to operate the handle to realize the bending adjustment function of the catheter, so it is difficult to control the handle and the guide wire at the same time. It can only firstly adjust and lock the bending angle of the head end of the tube by means of the handle, judge the approximate pointing direction of the head end of the tube according to DSA imaging technology, and then control the guide wire to tentatively enter the target blood vessel. If the target blood vessel has a complex structure, then it is difficult to determine whether the head end of the tube is aligned with the inlet of the target blood vessel. As such, it is necessary to repeatedly switch between the control of the handle and the control of the guide wire, and the bending angle of the head end of the tube cannot be adjusted synchronously with the control of the guide wire. The efficiency of the guide wire to tentatively enter the target blood vessel is low and thus the operation time is prolonged.

There is another steerable catheter provided with a Y-shaped bifurcated handle in the prior art, where the Y-shaped handle has no appropriate holding portion, the handle driving portion is located below the tube and the guide-wire accessing hole, and the handle generally requires to be controlled by two hands. Generally, the left hand is adopted to fix the handle body, the right hand is adopted to control the driving portion to adjust the bending angle of the head end of the catheter, and it is also impossible to control the handle and the guide wire at the same time.

During a traditional superselective surgery, the operating habit of a doctor is: holding the catheter by the left hand, controlling the guide wire by the right hand, and adjusting the direction of advancement of the guide wire through repeated rotating the catheter and sliding the guide wire. However, the aforementioned steerable catheter of the prior art is only suitable for right-hand operation, and thus it does not conform to the operating habit of operating the catheter by the left hand and operating the guide wire by the right hand, and the angle and rotation direction of the catheter need to be repeatedly adjusted during the operation. It requires pushing the guide wire in each of the angles and directions and then determines whether the head end of the catheter is directed to the branch blood vessel by means of the advancement direction of the guide wire. If the steerable catheter is only suitable for right-hand operation, then it needs to use the right hand to adjust each angle and direction, and then push the guide wire by the right hand to observe the advancement direction of the guide wire, which takes a long time to operate; or it needs the two hands to operate alternatively. However, this does not meet the operating habit, and may bring greater hidden dangers.

SUMMARY

Solutions to the Problem

The technical problem to be solved by the present invention is that, in view of the defects of the prior art, a steerable catheter, of which the bending adjustment can be controlled by the left hand, is provided, which enables the left hand to control the handle and the right hand to control the guide wire, thus enabling the bending angle adjustment of the head end of the tube and the control of the guide wire to be simultaneous, and therefore increases the efficiency of the guide wire to tentatively enter a target blood vessel, simplifies the operation steps, enables an operator to superselect the target blood vessel more conveniently and quickly, shortens the surgical operation time, and reduces the radiation hazard of X-rays to a patient.

The technical solution adopted by the present invention to solve the technical problem thereof is as follows.

A steerable catheter suitable for left-hand operation, includes a tube through which a pull wire is threaded, a handle assembly, and a Luer connector, wherein:

the handle assembly includes a holding handle provided with an axial through cavity, a slide mechanism for pulling the pull wire, and a slide control mechanism for controlling an action of the slide mechanism;

a proximal end of the tube passes through the cavity of the holding handle to be connected with the Luer connector;

the slide mechanism includes a slide base body disposed in the cavity of the holding handle or in the slide control mechanism, and a slide member axially sliding along the holding handle and fitted on the slide base body, the slide member is fixedly connected to the pull wire;

the slide control mechanism includes a connecting member connected with the slide member, and a drive adjustment member connected with the connecting member and adjusting the position of the slide member, the drive adjustment member is provided at the proximal end of the holding handle for convenient left fingers operation.

In the steerable catheter suitable for left-hand operation, preferably the first technical solution is: the drive adjustment member includes a driving sleeve which is sleeved outside the slide member and engages with the slide member, and a knob disposed at a proximal end of the driving sleeve, the rotation of the knob enables the driving sleeve to rotate relatively to the holding handle and thus drives the slide member engaging with the driving sleeve to slide axially.

In the first technical solution, preferably the connecting member is a section of thread teeth disposed on the slide member, and a continuous thread groove disposed on an inner wall of the driving sleeve, and the thread teeth engage with the thread groove to lock the slide member when the driving sleeve does not rotate.

In the first technical solution, preferably the slide base body is provided with a sliding groove axially along the holding handle, the slide member is accommodated in the sliding groove and axially slides along the holding handle, and the length of the sliding groove satisfies that: the slide member slides in the sliding groove to pull the pull wire, thereby achieving a preset maximum adjustable bend angle at a distal end of the catheter.

In the first technical solution, preferably a position-limiting rib is disposed at a proximal end of an inner wall of the holding handle, a position-limiting groove is disposed on an outer wall of the driving sleeve correspondingly, the position-limiting rib is located in the position-limiting groove to limit the driving sleeve to only rotate relatively to the holding handle rather than axially move; or a position-limiting groove is disposed on the inner wall of the holding handle, a position-limiting rib is disposed on the outer wall of the driving sleeve correspondingly, the position-limiting rib is located in the position-limiting groove to limit the driving sleeve to only rotate relatively to the holding handle rather than axially move.

In the steerable catheter suitable for left-hand operation, preferably the second technical solution is: the drive adjustment member includes a hollow driving shell fixedly connected to the proximal end of the holding handle and a sliding button;

the slide member and the slide base body are disposed in the driving shell; and the driving shell is provided with an elongated adjusting groove axially, the sliding button is fitted in the elongated adjusting groove in a position-limiting manner to slide, and is connected to the slide member through the connecting member, and the sliding button drives the slide member to axially slide along the slide base body.

In the second technical solution, preferably the connecting member is an elastic body which radially expands and contracts along the holding handle;

a tooth slot is disposed on the inner wall of the driving shell, a toothed rack is disposed on the sliding button, and as driven by the elastic expansion of the connecting member, the toothed rack of the sliding button engages with the tooth slot of the driving shell to lock the slide member, and the sliding button is pressed to overcome the elastic force of the connecting member, so as to release the engagement lock of the toothed rack and the tooth slot and drive the slide member to slide.

In the second technical solution, preferably the slide base body is a sliding tube sleeved on the tube, and the slide member is wrapped outside the sliding tube to slide along the sliding tube.

In the second technical solution, preferably a position-limiting member is disposed on the top of the slide member, and the position-limiting member limits the sliding button to only move relatively to the slide member in a direction perpendicular to an axial direction of the holding handle, and to move simultaneously with the slide member in the axial direction of the holding handle.

In the steerable catheter suitable for left-hand operation, preferably the third technical solution is: the drive adjustment member includes a driving shell and a trigger bar;

the slide member and the slide base body are disposed in the driving shell, the trigger bar is rotationally connected on the slide base body, and one end of the trigger bar is a driving portion extending to the outside of the holding handle, and the other end of the trigger bar is a shifting portion for shifting the slide member to axially move along the slide base body; and the driving portion of the trigger bar is pulled back and forth on the axial direction of the holding handle and is located at an arbitrary position during being pulled, so as to drive the slide member to axially move along the slide base body and be located at a position.

In the third technical solution, preferably a rotating member is disposed at a middle portion of the trigger bar, a rotating hole is disposed on the slide base body correspondingly, the rotating member is socket-and-spigot jointed within the rotating hole to rotate, a guide groove is disposed on the slide base body along the axial direction of the holding handle, and the slide member, via a position-limiting post disposed on a side surface thereof, is fitted in the guide groove to axially slide along the holding handle.

In the third technical solution, preferably two position-limiting posts are disposed on the same side of the slide member with intervals, the shifting portion of the trigger bar is inserted between the two position-limiting posts and shift the two position-limiting posts to achieve the sliding of the slide member.

The present invention adopts the manner of disposing the slide control mechanism, especially the drive adjustment member at the proximal end of the holding handle for convenient left hand operation, i.e., between the holding handle and the guide-wire accessing hole (the Luer connector), which enables the left hand to control the handle and the right hand to control the guide wire conveniently, thus enabling the bending angle adjustment of the head end of the tube and the control of the guide wire to be simultaneous, and therefore increases the efficiency of the guide wire to tentatively enter a target blood vessel, simplifies the operation steps, enables an operator to superselect the target blood vessel more conveniently and quickly, shortens the surgical operation time, and reduces the radiation hazard of X-rays to a patient.

BRIEF DESCRIPTION OF THE DRAWINGS

The present invention will be further illustrated in connection with accompanying drawings and embodiments, in which.

DETAILED DESCRIPTION

For a better understanding of the technical features, the objects and the effects of the present invention, the specific embodiments of the present invention will be described in detail with reference to the accompanying drawings.

Embodiment 1, as shown in FIGS. 1-5, is the first technical solution of the present invention.

A steerable catheter suitable for left-hand operation includes a tube 1100 through which a pull wire is threaded, a handle assembly 1200, and a Luer connector 1300.

Figure 1:
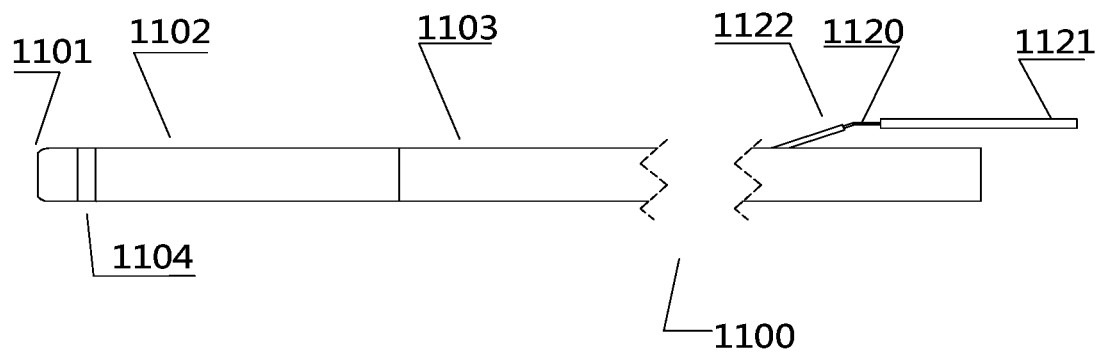
FIG. 1 is a schematic structural view of the tube according to embodiments 1-3 of the present invention.
Figure 2:
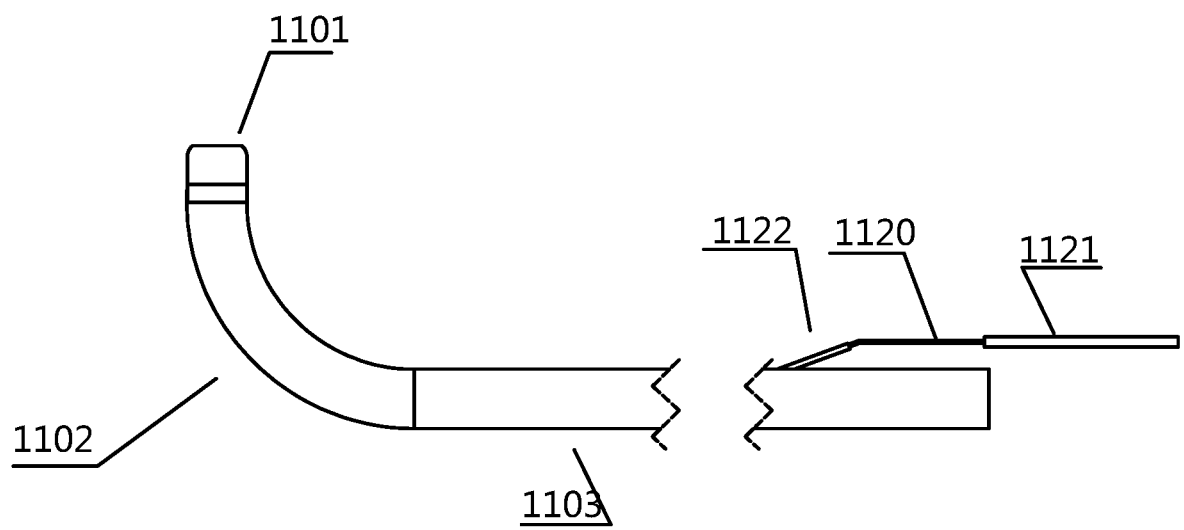
FIG. 2 is a schematic structural view of the tube according to the embodiments 1-3 of the present invention, after the distal end of the tube is bent.

As shown in FIG. 1, it is a schematic structural view of the tube 1100 under a non-bending state; and FIG. 2 shows a schematic structural view of the tube 1100 under an adjusted bending state. The tube 1100 is a woven mesh structure formed from polymer materials by hot-melt composite molding. The tube 1100 includes an elastic section 1102 disposed at a distal end thereof, which is freely bendable in a certain angle range and actively returns to the initial angular direction; and a longer and stiffer section 1103 connected to the proximal end of the elastic section 1102. A curved end 1101 having a smooth surface is disposed at the distal end of the elastic section 1102, and the curved end 1101 is used for reducing the damage of the distal end of the catheter to the inner wall of the human blood vessel. The tube 1100 is provided with at least one delivery cavity (not shown) and at least one filament cavity 1122, and the delivery cavity penetrates completely from the distal end of the tube 1100 to the proximal end of the tube 1100. The filament cavity 1122 is embedded within the wall of the tube 1100, and at least one anchoring ring 1104 is provided at the distal end of the filament cavity 1122. The pull wire 1120 is disposed within the filament cavity 1122, and the distal end of the pull wire 1120 is fixed onto the anchoring ring 1104 and is led out from a sidewall adjacent the proximal end of the tube 1100, along the filament cavity 1122.

In order to prevent the pull wire 1120 from being bent and deformed after exiting the filament cavity 1122, a portion of the pull wire 1120 that exits the tube 1100 is externally connected with a stiffening tube 1121. The stiffening tube 1121 is usually made of stainless steel and fixed with the pull wire 1120 in a compression joint or welding manner. As shown in FIG. 2, the stiffening tube 1121 is clamped and pulled tightly to generate a pulling force on the distal end of the tube 1100, such that the elastic section 1102 is bent within a certain angle range, and if the pulling force applied on the pull wire 1120 is taken off, the elastic section 1102 will return to the initial angular direction under the action of its own elasticity.

Figure 3A:
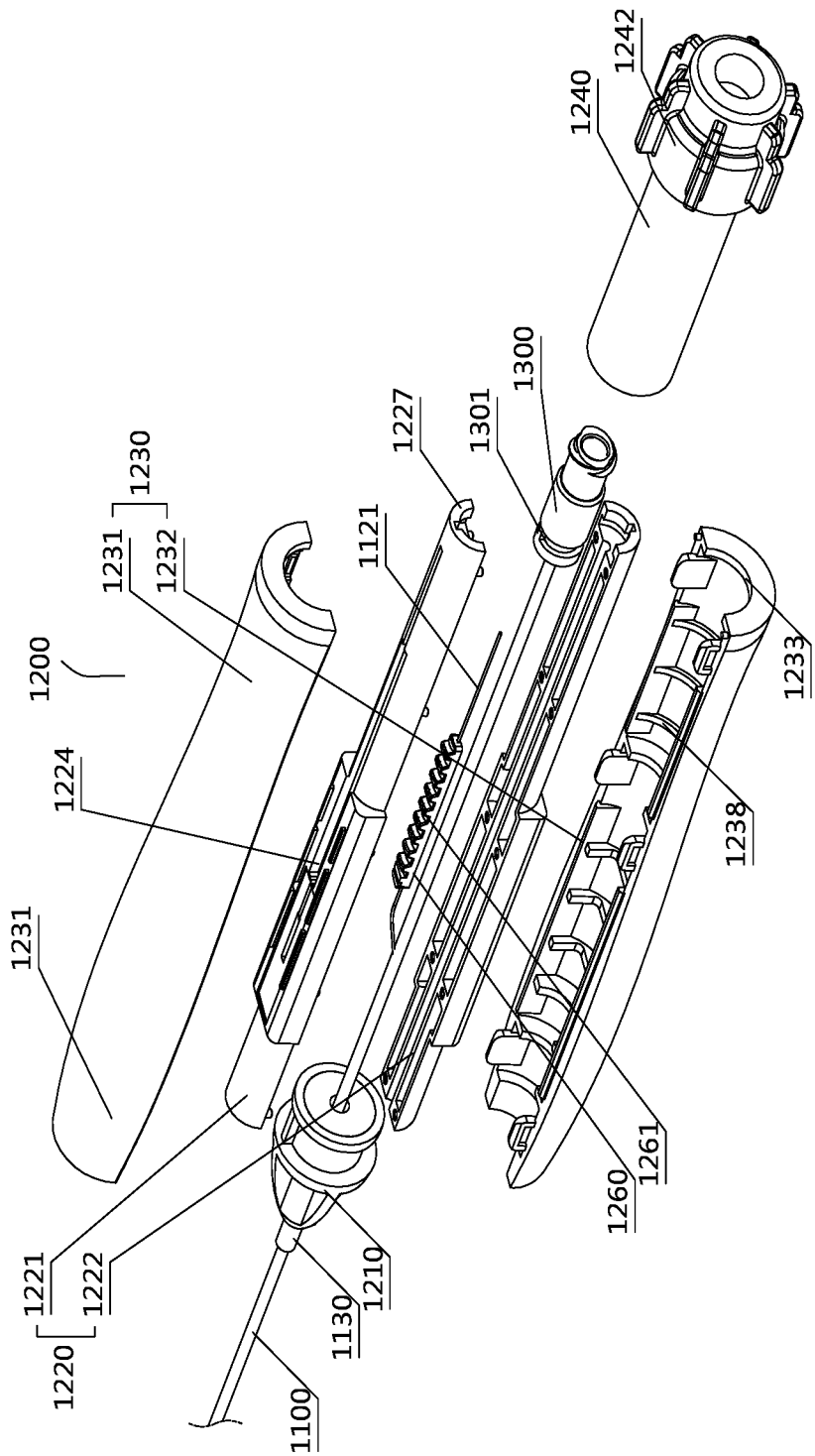
FIG. 3*a* is an exploded view showing the structure of the steerable catheter according to the first embodiment of the present invention along a direction at the proximal end of the steerable catheter.
Figure 3B:
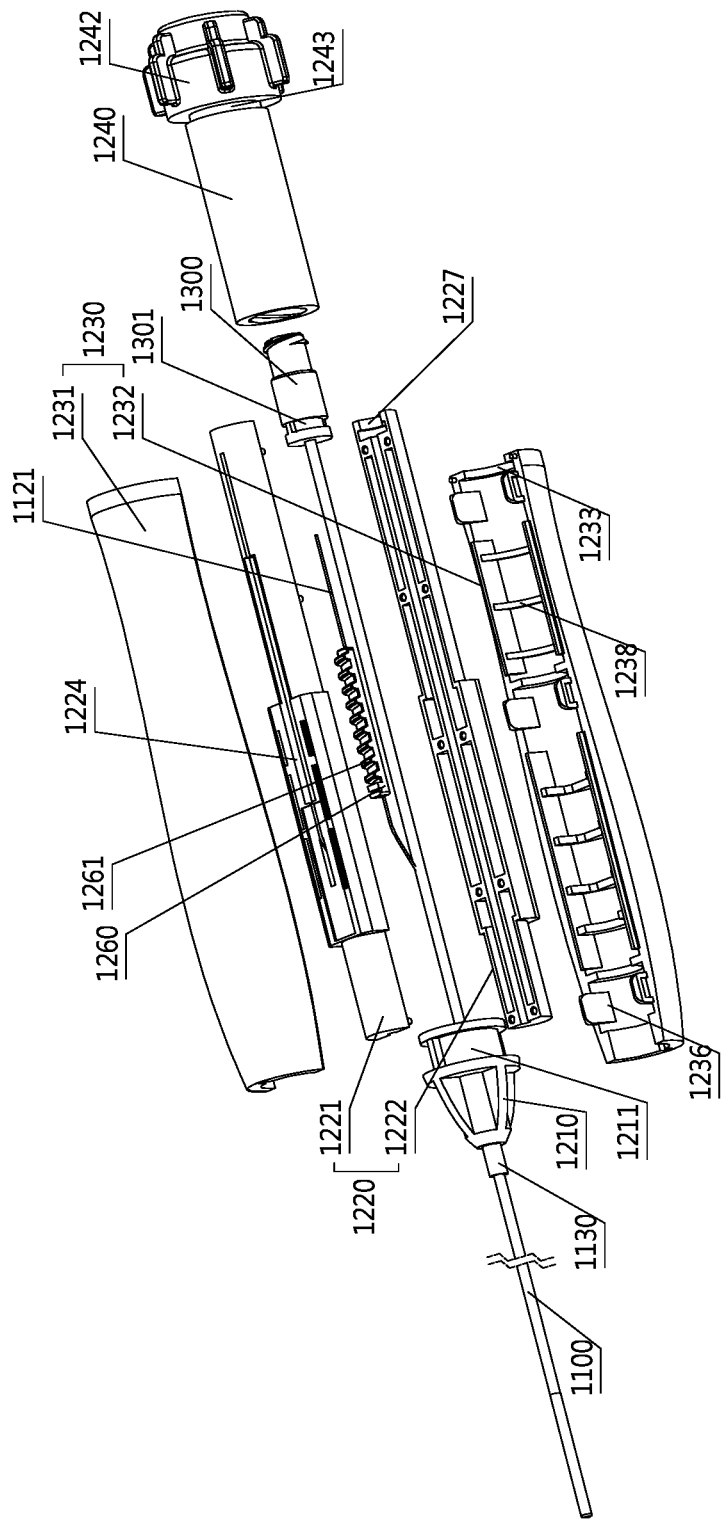
FIG. 3*b* is an exploded view showing the structure of the steerable catheter according to the first embodiment of the present invention along another direction at the proximal end of the steerable catheter.
Figure 4:
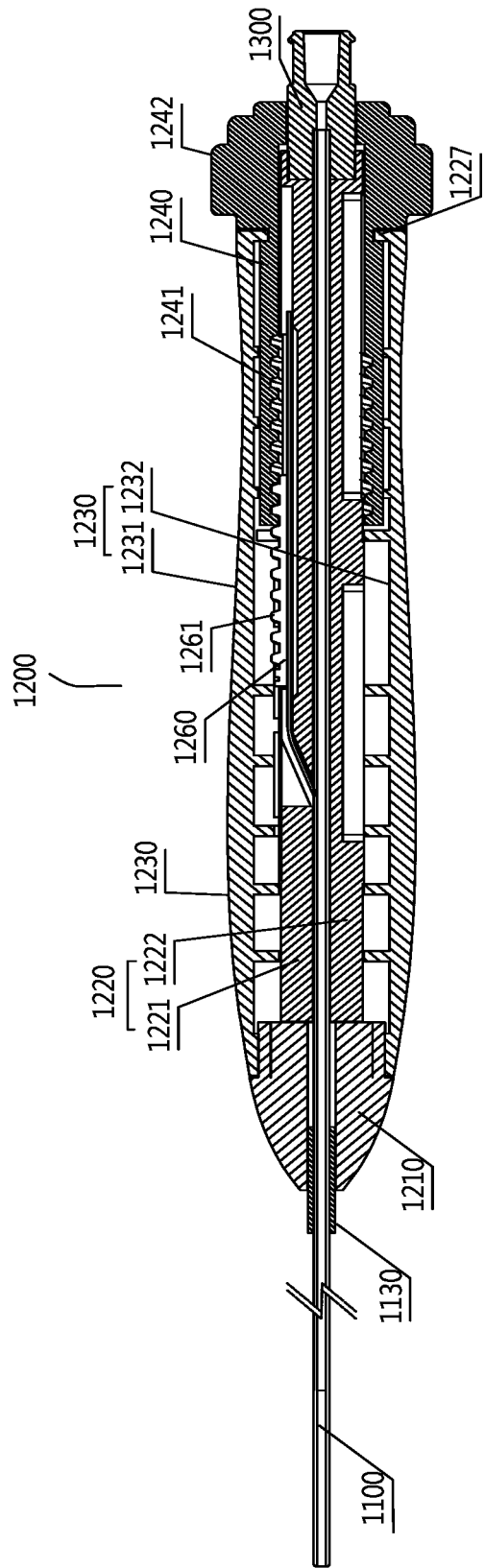
FIG. 4 is a cross-sectional view of the steerable catheter according to the first embodiment of the present invention.

As shown in FIGS. 3*a*-4, the handle assembly 1200 includes a holding handle 1230 provided with an axial through cavity, a slide mechanism for pulling the pull wire 1120, and a slide control mechanism for controlling an action of the slide mechanism; and a proximal end of the tube 1100 passes through the cavity of the holding handle 1230 to be connected to the Luer connector 1300.

The holding handle 1230 is used for holding by an operator, and is formed by fastening a male buckle housing 1232 to a female buckle housing 1231. The shape of the holding handle 1230 is set according to actual requirements, and is generally a columnar structure, but the shape is not limited hereto, as long as it conforms to ergonomics and it is convenient to hold and operate. In this embodiment, the holding handle 1230 has a length of 8-12 cm, and an outer diameter of 1.5-2 cm, which is suitable for the operator to hold and conforms to ergonomics.

An end cap 1210 is disposed at the distal end of the holding handle 1230, the end cap 1210 has an inner cavity for mounting the tube 1100, and the diameter of the inner cavity of the end cap 1210 should be slightly larger than the maximum diameter of the tube 1100. The tube 1100 is coated with a buffering tube 1130 at a portion where it is butt jointed with the end cap 1210, and the buffering tube 1130 may be formed by injection molding using a soft rubber material (silicon-rubber, TPU, etc.). When the proximal end of the tube 1100 is subjected to an acting force which is perpendicular to the tube 1100, the buffering tube 1130 can reduce a counter-acting force applied on the proximal end of the tube 1100, thereby avoiding the folding of the tube 1100.

The slide mechanism includes a slide base body 1220 disposed in the cavity of the holding handle 1230 or in the slide control mechanism, a slide member 1260 axially sliding along the holding handle 1230 and fitted on the slide base body 1220, and the slide member 1260 is fixedly connected to the pull wire 1120; the slide control mechanism includes a connecting member connected with the slide member 1260, and a drive adjustment member connected with the connecting member and adjusting the position of the slide member 1260, and the drive adjustment member is provided at the proximal end of the holding handle 1230 for facilitating left fingers operation.

In this embodiment, both the slide mechanism and the slide control mechanism are disposed in the cavity of the holding handle 1230, and snapping grooves surrounded by ribs 1238 are disposed with intervals on the inner wall of the holding handle 1230 and are used for assembling the slide base body 1220. A position-limiting protrusion 1236 is disposed on the distal end of the holding handle 1230, the end cap 1210 is disposed with a position-limiting groove 1211, the position-limiting protrusion 1236 is located in the position-limiting groove 1211 to fix the end cap 1210.

As shown in FIGS. 3a-4, the pull wire 1120 penetrates out from an inclined hole disposed within the slide base body 1220, and the stiffening tube 1121 disposed at the proximal end of the pull wire 1120 is fixedly connected with the slide member 1260. The slide member 1260 connects with the driving sleeve 1240 through thread, and the driving sleeve 1240 and the end cap 1210 are respectively disposed on the proximal end and the distal end of the holding handle 1230. The holding handle 1230 is formed by fastening a male buckle housing 1232 to a female buckle housing 1231, and the slide base body 1220 is formed by fastening a male buckle pedestal 1221 to a female buckle pedestal 1222.

The slide base body 1220 is generally formed by one-step injection molding using a hard rubber plastic (ABS, POM, etc.) or by machining. Since the slide base body 1220 is disposed in the holding handle 1230, the slide base body 1220 is axially disposed along the holding handle 1230 and has a shape that may be consistent with or different from that of the holding handle 1230. For example, the cross-section of the holding handle 1230 is of a curved shape such as a circle, an oval and the like, and the cross-section of the slide base body 1220 may be of a curved shape such as a circle, an oval and the like, or alternatively may have a polygonal structure such as a square, a trapezoid, and the like. The slide base body 1220 is provided with an inner cavity for installing the proximal end of the tube 1100 to be connected with the Luer connector 1300, and the diameter of the inner cavity should be slightly larger than that at the proximal end of the tube 1100. A position-limiting rib 1227 is disposed at the proximal end of the slide base body 1220, a position-limiting groove 1301 is disposed on the Luer connector 1300 correspondingly, and the position-limiting rib 1227 is fitted with the position-limiting groove 1301 to fix the Luer connector 1300.

As shown in FIGS. 3a-4, the slide base body 1220 is provided with a sliding groove 1224 axially along the holding handle 1230, the slide member 1260 is accommodated in the sliding groove 1224 and axially slides along the holding handle 1230, and the length of the sliding groove 1224 satisfies that: the slide member 1260 slides in the sliding groove 1224 to pull the pull wire 1120, thereby achieving a preset maximum adjustable bend angle at a distal end of the catheter. That is, the maximum bending angle of the distal end of the tube 1100 can be determined by setting the length of the sliding groove 1224. For example, for the bending of the distal end of the tube 1100 from 0° to 180°, it needs to pull the pull wire 1120 by a distance of 15 mm, and then the sliding length of the slide member 1260 in the sliding groove 1224 is set as 15 mm, and as such the maximum adjustable bend angle of the distal end of the tube 1100 is limited to 180°. The width of the sliding groove 1224 should be slightly larger than that of the slide member 1260. An inclined hole is disposed between a bottom surface of the sliding groove 1224 and a wire outgoing point of the pull wire, for facilitating the pull wire to pass through the inclined hole into the sliding groove 1224 and then the pull wire is fixedly connected with the slide member 1260. A slot (not shown) is provided at a sliding surface on which the slide member 1260 contacts the sliding groove 1224, for fixing the stiffening tube 1121 disposed at the proximal end of the pull wire. The stiffening tube 1121 is typically fixed in the slot by welding, so that the proximal end of the pull wire is fixed onto the slide member 1260.

As shown in FIGS. 3a-4, the slide member 1260 may be made of metal or polymer materials, the shape of the slide member 1260 is not limited, and is preferably an elongated structure which is convenient for setting a length of thread on the slide member 1260. The slide member 1260 is placed in the sliding groove 1224, and kept in planar contact with the bottom of the sliding groove 1224.

The drive adjustment member includes a driving sleeve 1240 which is sleeved outside the slide member 1260 and engages with the slide member 1260, and a knob 1242 disposed at a proximal end of the driving sleeve 1240, the rotation of the knob 1242 enables the driving sleeve 1240 to rotate relatively to the holding handle 1230 and thus drives the slide member 1260 engaging with the driving sleeve 1240 to slide axially. The knob 1242 is coaxial with the driving sleeve 1240, and a protrusion or flange is disposed on the outer wall of the knob 1242 for facilitating the rotation with fingers.

As shown in FIGS. 3a-4, the connecting member is a section of thread teeth 1261 disposed on the slide member 1260, and a continuous thread groove 1241 disposed on an inner wall of the driving sleeve 1240, and the thread teeth 1261 engage with the thread groove 1241 to lock the slide member 1260 when the driving sleeve 1240 does not rotate. Particularly, the section of thread teeth 1261 is disposed at the external side of the slide member 1260, i.e., on the top surface of the slide member 1260, and the thread teeth 1261 has the same thread pitch with that of the thread groove 1241 disposed on the inner wall of the driving sleeve 1240. The thread groove 1241 engages with the thread teeth 1261, so as to limit the sliding direction of the slide member 1260 together with the driving sleeve 1240 and the sliding groove 1224 of the slide base body 1220. When the knob 1242 disposed at the proximal end of the driving sleeve 1240 is rotated, the slide member 1260 axially slides along the sliding groove 1224, and does not deflect radially. As the rotation of the knob 1242 is stopped, the thread groove 1241 disposed on the inner wall of the driving sleeve 1240 tightly engages with the thread teeth 1261 disposed on the top surface of the slide member 1260 to form a static friction force, so as to prevent the movement of the slide member 1260, and fix the slide member 1260 at a preset position, thereby realizing the locking of the bending angle of the distal end of the tube 1100. The length of the driving sleeve 1240 and the length of the thread groove 1241 are associated with the moving distance of the slide member 1260, and meet the achievement of the adjustment of the maximum bending angle of the distal end of the steerable catheter.

As shown in FIGS. 3a-4, a position-limiting rib 1233 is provided at the proximal end of the holding handle 1230, a position-limiting groove 1243 is disposed on the outer wall of the driving sleeve 1240 correspondingly, and the position-limiting rib 1233 is located in the position-limiting groove 1243 to limit the driving sleeve 1240 to only rotate relatively to the holding handle rather than axially move. Alternatively, a position-limiting groove is disposed on the inner wall of the holding handle 1230, a position-limiting rib is disposed on the outer wall of the driving sleeve 1240 correspondingly, and the position-limiting rib is located in the position-limiting groove to limit the driving sleeve 1240 to only rotate relatively to the holding handle 1230 rather than axially move.

Figure 5:
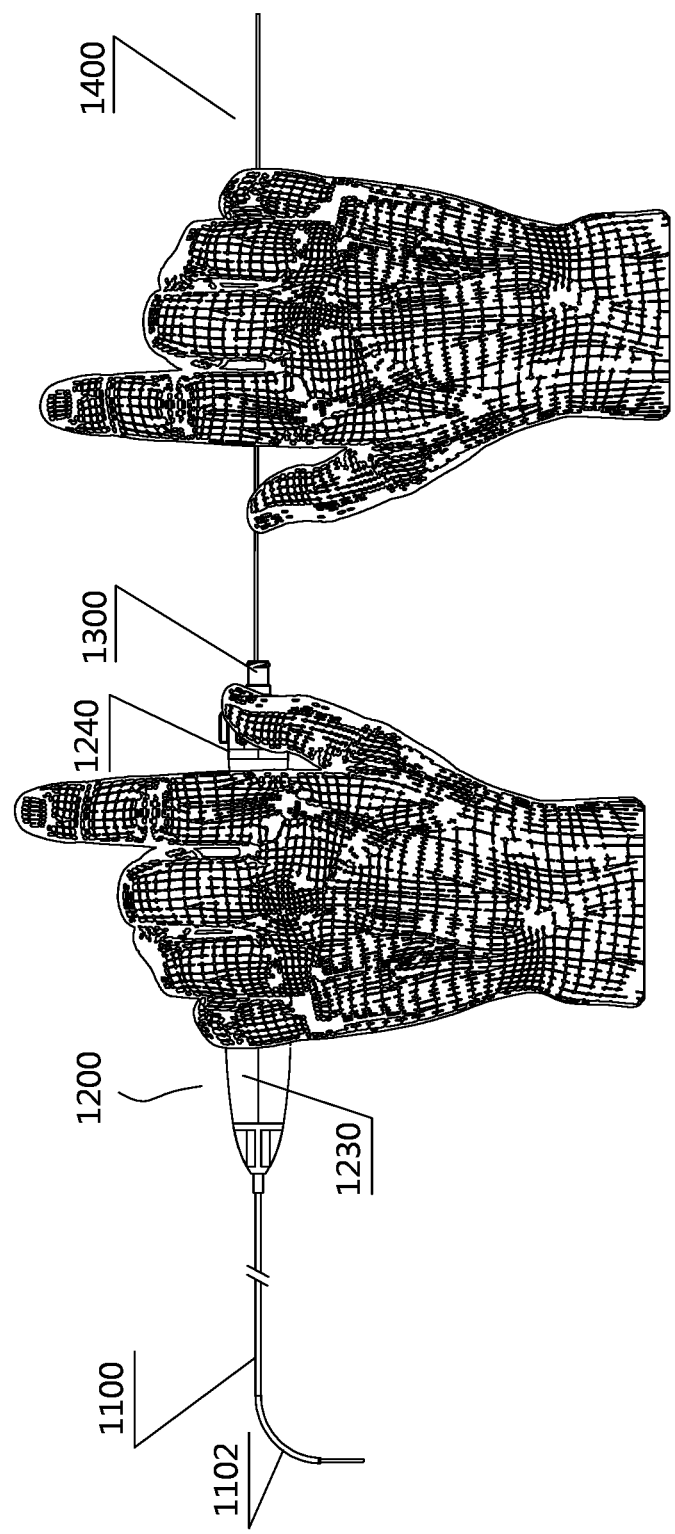
FIG. 5 is a schematic view showing the operation of the steerable catheter according to the first embodiment of the present invention.

The operation manner of the steerable catheter of this embodiment is as shown in FIG. 5: the steerable catheter includes a tube 1100, a handle assembly 1200, a Luer connector 1300, the holding handle 1230 of the handle assembly 1200 is held in the left hand, the driving sleeve 1240 located at the right side of the holding handle is rotated clockwise (which is alternatively set as counterclockwise) by fingers of the left hand to release the self-locking state of the slide member, and the driving sleeve 1240 is further rotated to move the slide member axially along the slide base body, thereby achieving a function of adjusting the bending of the elastic section 1102 located at the distal end of the tube 1100. As the rotation of the driving sleeve 1240 is stopped, the elastic section 1102 will be locked at a preset bending angle, and the guide wire 1400 enters the target blood vessel as controlled by the right hand.

Figure 6:
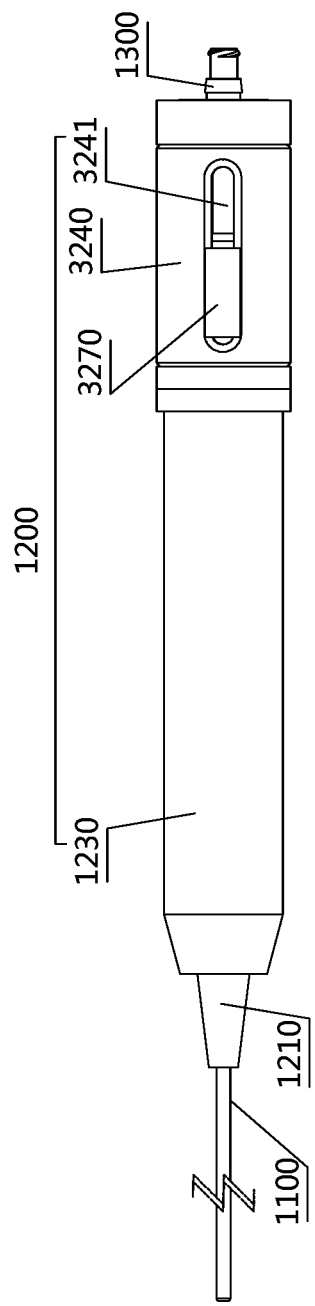
FIG. 6 is a schematic view showing the appearance of the handle assembly of the steerable catheter according to the second embodiment of the present invention.
Figure 7A:
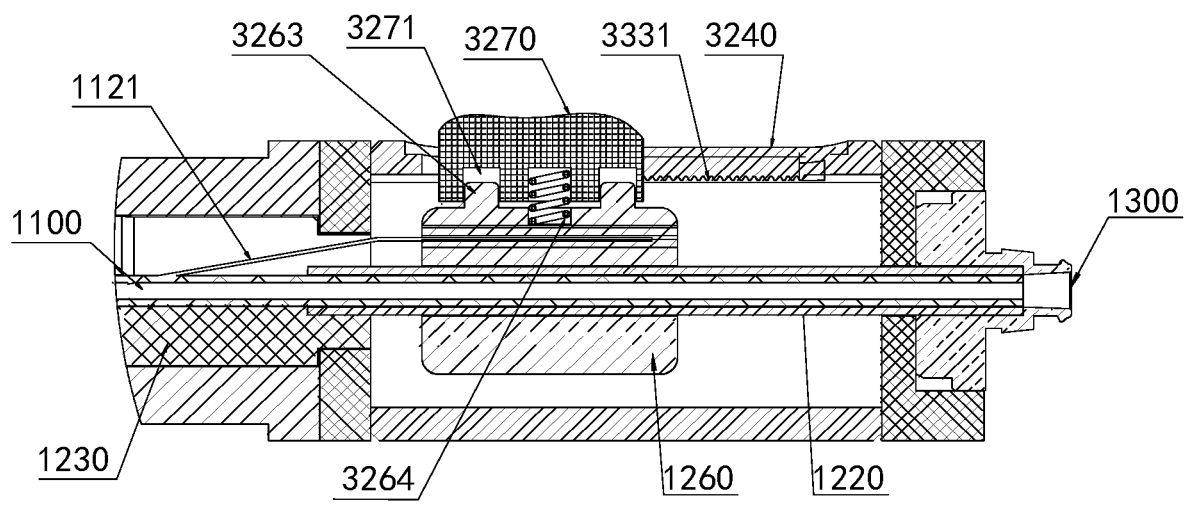
FIG. 7*a* is an axial cross-sectional view of the handle assembly of the steerable catheter according to the second embodiment of the present invention.
Figure 7B:
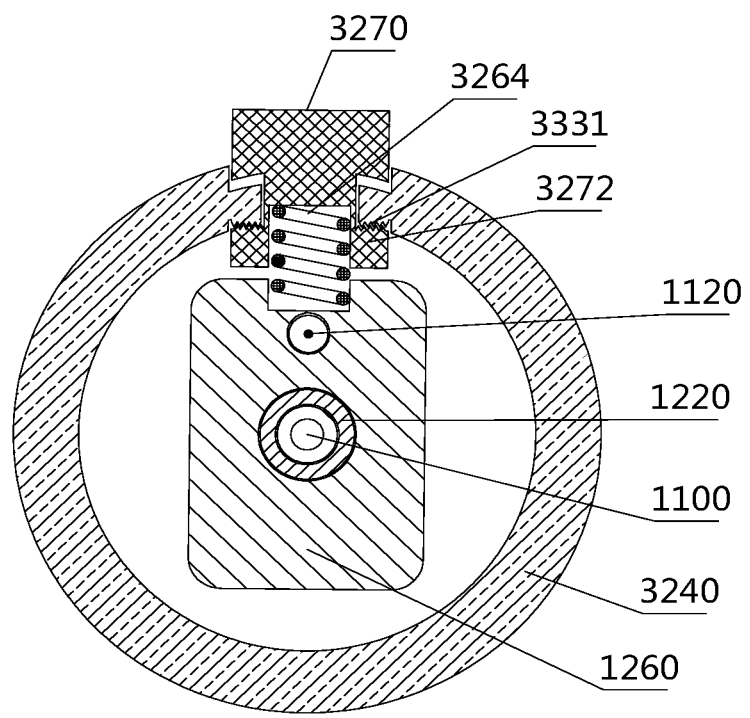
FIG. 7*b* is a radial cross-sectional view of the handle assembly of the steerable catheter according to the second embodiment of the present invention.
Figure 8:
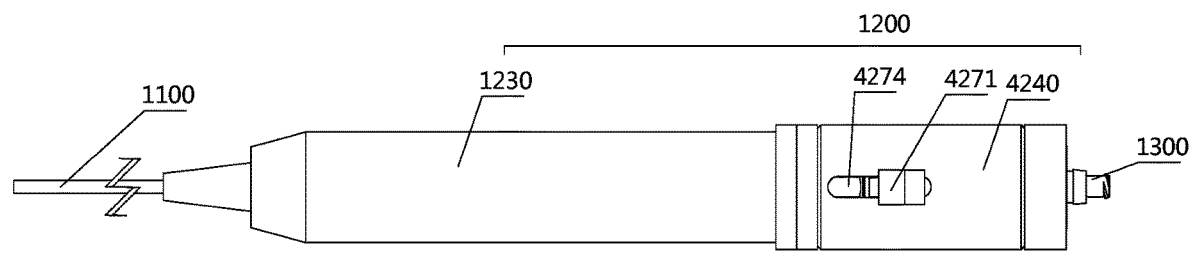
FIG. 8 is a schematic view showing the appearance of the handle assembly of the steerable catheter according to the third embodiment of the present invention.
Figure 9:
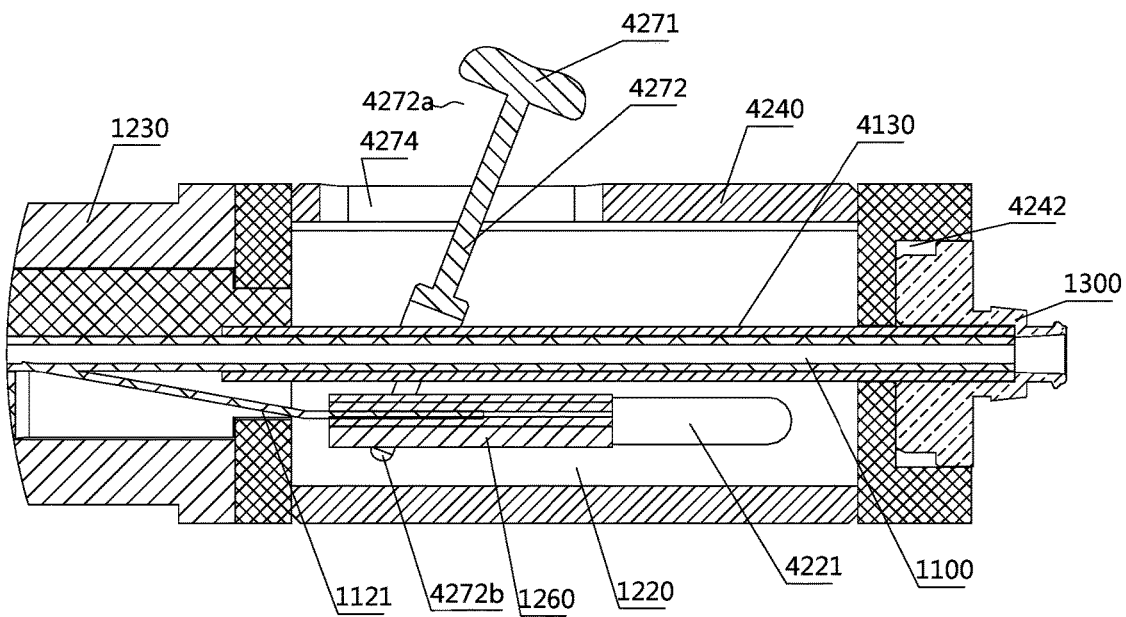
FIG. 9 is a cross-sectional view of the handle assembly of the steerable catheter according to the third embodiment of the present invention.
Figure 10:
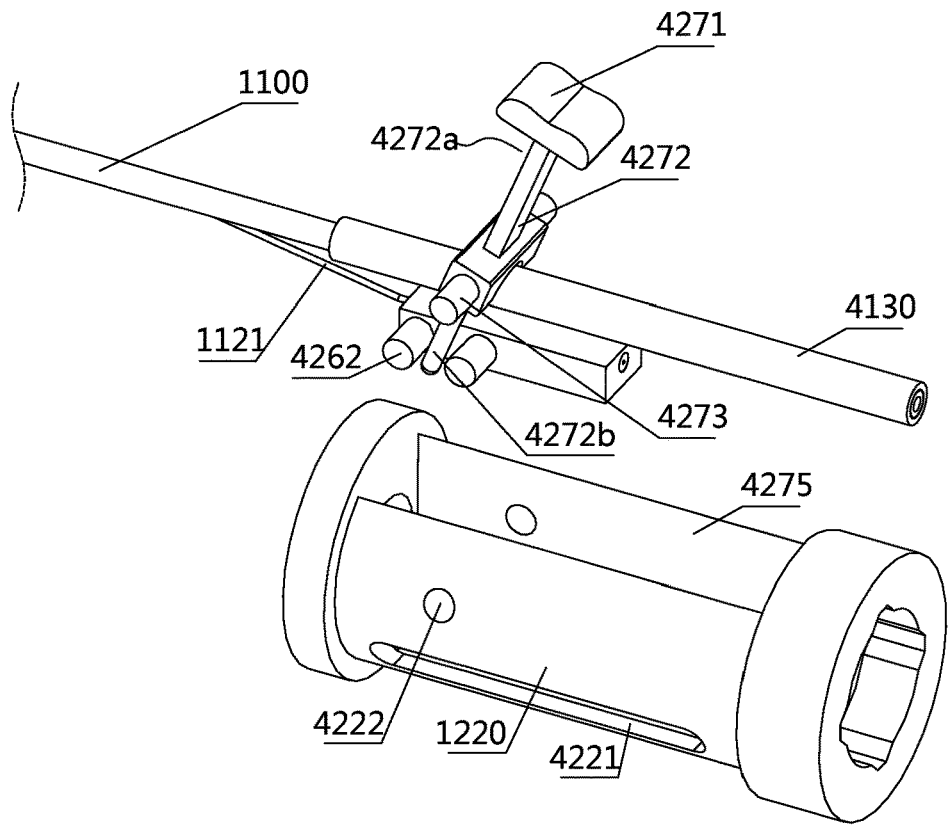
FIG. 10 is an exploded view of the assembly of the drive adjustment member and the slide member according to the third embodiment of the present invention.
Figure 11:
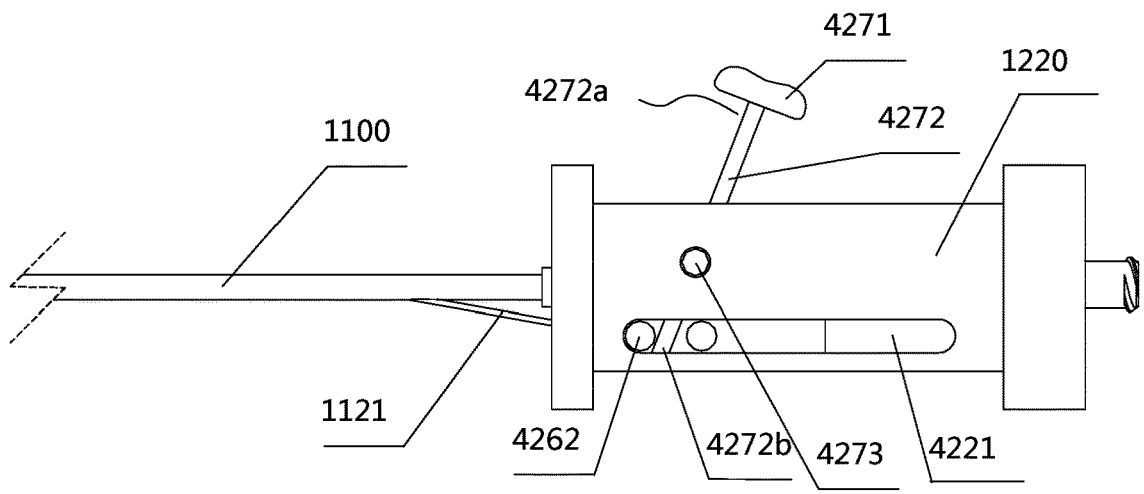
FIG. 11 is an assembly diagram of the drive adjustment member and the slide member according to the third embodiment of the present invention.

Embodiment 2, as shown in FIGS. 6-7b, is a second implementation of the steerable catheter suitable for left-hand operation, which includes a tube 1100 through which a pull wire is threaded, a handle assembly 1200, and a Luer connector 1300. The handle assembly 1200 includes a holding handle 1230 provided with an axial through cavity, a slide mechanism for pulling the pull wire, and a slide control mechanism for controlling an action of the slide mechanism; and a proximal end of the tube 1100 passes through the cavity of the holding handle 1230 to be connected to the Luer connector 1300.

The structure of the tube 1100 is the same as that of embodiment 1, and thus will not be repeated anymore here.

The structure of the holding handle 1230 is the same as that of embodiment 1, and thus will not be repeated anymore here.

As shown in FIGS. 6-7b, the slide mechanism includes a slide base body 1220 disposed in the slide control mechanism, a slide member 1260 axially sliding along the holding handle 1230 and fitted on the slide base body 1220, and the slide member 1260 is fixedly connected to the stiffening tube 1121 of the pull wire, where the fixation manner of the slide member 1260 and the stiffening tube 1121 is the same as that of embodiment 1, and thus will not be repeated anymore here; and the slide control mechanism includes a connecting member 3264 connected with the slide member 1260, and a drive adjustment member connected with the connecting member 3264 and adjusting the position of the slide member 1260, and the drive adjustment member is provided at the proximal end of the holding handle for facilitating left fingers operation.

As shown in FIGS. 6-7b, in this embodiment, the drive adjustment member includes a hollow driving shell 3240 fixedly connected to the proximal end of the holding handle 1230 and a sliding button 3270. The slide member 1260 is disposed in the driving shell 3240; and the driving shell 3240 is provided with an elongated adjusting groove 3241 axially, the sliding button 3270 is fitted in the elongated adjusting groove 3241 in a position-limiting manner to slide, and is connected to the slide member 1260 through the connecting member 3264, and the sliding button 3270 drives the slide member 1260 to axially slide along the slide base body 1220. The connecting member 3264 is an elastic body which radially expands and contracts along the holding handle, and in this embodiment the elastic body is a coil spring, also it may be other elastic bodies other than the coil spring, such as a pressure spring, a spring strip, and the like elastic bodies made from various materials which can spring back after being compressed, and the sliding button 3270 is fixedly connected with the slide member 1260 through the connecting member 3264; and a tooth slot 3331 is disposed on the inner wall of the driving shell 3240, and a toothed rack 3272 is disposed on the sliding button 3270, where under the elastic stretching action of the elastic body serving as the connecting member 3264, the toothed rack 3272 of the sliding button 3270 engages with the tooth slot 3331 of the driving shell 3240 to lock the slide member 1260, and the sliding button 3270 is pressed against the elastic force of the connecting member 3264, so as to release the engagement locking between the toothed rack 3272 and the tooth slot 3331 and drive the slide member 1260 to slide. Particularly, the surface of the sliding button 3270 is a concave cambered surface, which facilitates the thumb to press the slide button 3270 and push the slide button 3270 to move along the elongated adjusting groove 3241.

As shown in FIGS. 6-7b, the slide base body 1220 is a sliding tube sleeved on the tube 1100, and the slide member 1260 is wrapped on and slides on the sliding tube. The sliding tube is a metal tube which is sleeved outside the tube 1100 and disposed in a region from the holding handle 1230 to the Luer connector 1300. This metal tube is used for stiffening the tube 1100, has a smooth surface, and axially passes through an inner cavity of the slide member 1260. Therefore, during the axial moving of the slide member 1260 along the metal tube, the straight shape of the tube 1100 is not influenced.

As shown in FIGS. 6-7b, a position-limiting member 3263 is disposed on the top of the slide member 1260, in this embodiment the position-limiting member 3263 is a convex column as set, a locating groove 3271 is disposed on the sliding button 3270 correspondingly, and the locating groove 3271 corresponds to the convex column to limit the position of the sliding button 3270 on the slide member 1260. The position-limiting member 3263 limits the sliding button 3270 to only move relatively to the slide member 1260 in a direction perpendicular to an axial direction of the holding handle 1230, and to move simultaneously with the slide member 1260 in the axial direction.

The operation manner of this embodiment is that: the holding handle 1230 is held in the left hand, and the sliding button 3270 is pressed by the left hand to separate a pair of toothed racks 3272 on the bottom of the sliding button 3270 from the tooth slot 3331 on the inner wall of the driving shell 3240, and at this time, the sliding button 3270 can move left and right to drive the axial movement of the slide member 1260 along the holding handle 1230, and then the pull wire 1120 fixed to the slide member 1260 can pull or loosen the distal end of the tube 1100, thereby realizing free bending of the elastic section. If the pressing force applied on the sliding button 3270 is withdrawn, the sliding button 3270 is bounced towards the external side of the driving shell 3240 under the tension of the elastic body and is locked onto the driving shell 3240 by means of the engagement between the teeth of the toothed rack 3272 and the tooth slot 3331, and the slide member 1260 is fixed and stops moving as limited by the locating groove 3271, such that the elastic section at the distal end of the tube 1100 can lock a preset bending angle.

Embodiment 3, as shown in FIGS. 8-11, is a third implementation of the steerable catheter suitable for left-hand operation, which includes a tube 1100 through which a pull wire is threaded, a handle assembly 1200, and a Luer connector 1300. The handle assembly 1200 includes a holding handle 1230 provided with an axial through cavity, a slide mechanism for pulling the pull wire, and a slide control mechanism for controlling an action of the slide mechanism; and a proximal end of the tube 1100 passes through the cavity of the holding handle 1230 to be connected to the Luer connector 1300.

The structure of the tube 1100 is the same as that of embodiment 1, and thus will not be repeated anymore here.

The structure of the holding handle 1230 is the same as that of embodiment 1, and thus will not be repeated anymore here.

The slide mechanism includes a slide base body 1220 disposed in the slide control mechanism, a slide member 1260 axially sliding along the holding handle 1230 and fitted on the slide base body 1220, and the slide member 1260 is fixedly connected to the stiffening tube 1121 fixed on the pull wire; the slide control mechanism includes a connecting member connected with the slide member 1260, and a drive adjustment member connected with the connecting member and adjusting the position of the slide member 1260, and the drive adjustment member is provided at the proximal end of the holding handle 1230 for facilitating left fingers operation. The slide base body 1220 is a hollow columnar structure or the columnar structure of an accommodating groove 4275, and the accommodating groove 4275 is used for accommodating the slide control mechanism.

The drive adjustment member includes a driving shell 4240, and a trigger bar 4272; and the driving shell 4240 is fixed at the proximal end of the holding handle 1230, and has a shape consistent with that of the holding handle 1230. The proximal end of the driving shell 4240 is connected with the Luer connector 1300, and the particular connection manner is that: an accommodating groove 4242 is disposed at the proximal end of the driving shell 4240, and the Luer connector 1300 is located in the accommodating groove 4242.

The slide member 1260 and the slide base body 1220 are disposed in the driving shell 4240, the trigger bar 4272 is rotationally connected on the slide base body 1220, and one end of the trigger bar 4272 is a driving portion 4272*a* extending to the outside of the holding handle 1230, and the other end of the trigger bar 4272 is a shifting portion 4272*b* which shifts the slide member 1260 to axially move along the slide base body 1220; an side surface of the driving shell 4240 is provided with an elongated groove 4274 that corresponds to the accommodating groove 4275 of the slide base body 1220, and the driving portion of the trigger bar 4272 protrudes from the accommodating groove 4275 and the elongated groove 4274 for operating the trigger bar 4272 manually. For convenience of operation, the driving portion 4272*a* of the trigger bar 4272 is provided with a trigger cap 4271. The shape of the trigger cap 4271 is not limited, as long as the shape is convenient for holding in hand, and generally the trigger cap 4271 is spherical-shaped, strip-shaped or the like.

Since the Luer connector 1300 is located at the proximal end of the driving shell 4240, the tube 1100 passes through the driving shell 4240 to be connected with the Luer connector 1300, and a metal tube 4130 is sleeved outside the tube 1100 in the driving shell 4240 for strengthening.

A rotating member 4273 is disposed at the middle portion of the trigger bar 4272, a rotating hole 4222 is disposed on the slide base body 1220 correspondingly, the rotating member 4273 is inserted in the rotating hole 4222 and is rotated in the rotating hole 4222, the rotating member 4273 is preferably a rotating shaft, the slide member 1260 is disposed below the tube 1100, and then two parallel shifting portions 4272*b* are disposed on the lower portion of the trigger bar 4272 to respectively be socket-and-spigot jointed with the slide member 1260 from two sides of the tube 1100. The external side of each trigger bar 4272 is provided with a rotating shaft serving as the rotating member 4273, the two rotating shafts are coaxial, and two rotating holes 4222 are disposed on the slide base body 1220 correspondingly.

The slide base body 1220 is provided with a guide groove 4221 along the axial direction of the holding handle 1230, the connecting member connected with the slide member 1260 is a position-limiting post 4262 that is disposed on the side surface of the slide member 1260, and the slide member 1260 is fitted in the guide groove 4221 by means of the position-limiting post 4262 disposed on the side surface thereof, so as to axially slide along the holding handle 1230. Two position-limiting posts 4262 are disposed on the same side of the slide member 1260 with intervals, the shifting portion 4272*b* of the trigger bar 4272 is inserted between the two position-limiting posts 4262 and shift the two position-limiting posts 4262 to achieve the sliding of the slide member 1260.

The driving portion 4272*a* of the trigger bar 4272 is pulled back and forth on the axial direction of the holding handle 1230 and is located at a point, and the shifting portion 4272*b* of the trigger bar 4272 shifts the two position-limiting posts 4262 to drive the slide member 1260 to axially move along the slide base body 1220 and be located at a position.

The invention claimed is:

1. A steerable catheter for left-hand operation, comprising a tube through which a pull wire is threaded, a handle assembly, and a Luer connector, wherein:
   the handle assembly comprises a holding handle provided with an axial through cavity, a slide mechanism for pulling the pull wire, and a slide control mechanism for controlling an action of the slide mechanism;
   a proximal end of the tube passes through the cavity of the holding handle to be connected with the Luer connector;
   the slide mechanism comprises a slide base body disposed in the cavity of the holding handle or in the slide control mechanism, and a slide member axially sliding along the holding handle and fitted on the slide base body, the slide member is fixedly connected to the pull wire;
   the slide control mechanism comprises a connecting member connected with the slide member, and a drive adjustment member connected with the connecting member and adjusting the position of the slide member, the drive adjustment member is provided at the proximal end of the holding handle for the left-hand operation of left thumb when the holding handle is held by a user with left dorsum facing the user;
   wherein the drive adjustment member comprises a driving sleeve which is sleeved outside the slide member and engages with the slide member, and a knob disposed at a proximal end of the driving sleeve, the rotation of the knob enables the driving sleeve to rotate relatively to the holding handle and thus drives the slide member engaging with the driving sleeve to slide axially;
   wherein the driving sleeve which is located at a right side of the holding handle is rotated clockwise or counter-clockwise by the left fingers to release a self-locking state of the slide member, and the driving sleeve is further rotated to move the slide member axially along the slide base body, thereby achieving a function of adjusting bending of an elastic section which is located at a distal end of the tube, wherein the elastic section is locked at a preset bending angle when the rotation of the driving sleeve is stopped, and a guide wire enters a target blood vessel as controlled by the right hand;
   a position-limiting rib is disposed at a proximal end of the slide base body, a position-limiting groove is disposed on the Luer connector correspondingly, and the position-limiting rib is fitted with the position-limiting groove to fix the Luer connector.

2. The steerable catheter for left-hand operation of claim 1, wherein the connecting member is a section of thread teeth disposed on the slide member, and a continuous thread groove disposed on an inner wall of the driving sleeve, and the thread teeth engage with the thread groove to lock the slide member when the driving sleeve does not rotate.

3. The steerable catheter for left-hand operation of claim 1, wherein the slide base body is provided with a sliding groove axially along the holding handle, the slide member is accommodated in the sliding groove and axially slides along the holding handle, and the length of the sliding groove satisfies that: the slide member slides in the sliding groove to pull the pull wire, thereby achieving a preset maximum adjustable bend angle at a distal end of the catheter.

4. The steerable catheter for left-hand operation of claim 1, wherein a second position-limiting rib is disposed at a proximal end of an inner wall of the holding handle, a second position-limiting groove is disposed on an outer wall of the driving sleeve correspondingly, the second position-limiting rib is located in the second position-limiting groove to limit the driving sleeve to only rotate relatively to the holding handle rather than axially move; or the second position-limiting groove is disposed on the inner wall of the holding handle, the second position-limiting rib is disposed on the outer wall of the driving sleeve correspondingly, the second position-limiting rib is located in the second position-limiting groove to limit the driving sleeve to only rotate relatively to the holding handle rather than axially move.

5. The steerable catheter for left-hand operation of claim 1, wherein a portion of the pull wire that exits the tube is externally connected with a stiffening tube.

6. The steerable catheter for left-hand operation of claim 1, wherein the tube is coated with a buffering tube at a portion where it is butt jointed with an end cap, wherein the end cap is disposed at a distal end of the holding handle.

7. The steerable catheter for left-hand operation of claim 1, wherein the slide base body is formed by fastening a male buckle pedestal to a female buckle pedestal.

8. A steerable catheter for left-hand operation, comprising a tube through which a pull wire is threaded, a handle assembly, and a Luer connector, wherein:

the handle assembly comprises a holding handle provided with an axial through cavity, a slide mechanism for pulling the pull wire, and a slide control mechanism for controlling an action of the slide mechanism;

a proximal end of the tube passes through the cavity of the holding handle to be connected with the Luer connector;

the slide mechanism comprises a slide base body disposed in the cavity of the holding handle or in the slide control mechanism, and a slide member axially sliding along the holding handle and fitted on the slide base body, the slide member is fixedly connected to the pull wire;

the slide control mechanism comprises a connecting member connected with the slide member, and a drive adjustment member connected with the connecting member and adjusting the position of the slide member, the drive adjustment member is provided at the proximal end of the holding handle for the left-hand operation of left fingers when the holding handle is held by a user with left dorsum facing the user;

during operation, the left hand holds the holding handle and the left thumb is adjacent to the proximal end of the holding handle and operates the drive adjustment member, the right hand controls a guide wire, thus enabling a bending angle adjustment of a head end of the tube and a control of the guide wire at the same time;

a position-limiting rib is disposed at a proximal end of the slide base body, a position-limiting groove is disposed on the Luer connector correspondingly, and the position-limiting rib is fitted with the position-limiting groove to fix the Luer connector.

9. The steerable catheter for left-hand operation of claim 8, wherein a portion of the pull wire that exits the tube is externally connected with a stiffening tube.

10. The steerable catheter for left-hand operation of claim 8, wherein the tube is coated with a buffering tube at a portion where it is butt jointed with an end cap, wherein the end cap is disposed at a distal end of the holding handle.

11. The steerable catheter for left-hand operation of claim 8, wherein the slide base body is formed by fastening a male buckle pedestal to a female buckle pedestal.

* * * * *